US010398869B2

(12) United States Patent
Khabiri et al.

(10) Patent No.: US 10,398,869 B2
(45) Date of Patent: Sep. 3, 2019

(54) OXYGEN DELIVERY AND VENTILATION MONITORING SYSTEMS

(71) Applicants: Babak Khabiri, Columbus, OH (US); Nestor Millan Narcelles, Columbus, OH (US); Scott Meyers Cooper, Utica, OH (US)

(72) Inventors: Babak Khabiri, Columbus, OH (US); Nestor Millan Narcelles, Columbus, OH (US); Scott Meyers Cooper, Utica, OH (US)

( * ) Notice: Subject to any disclaimer, the term of this patent is extended or adjusted under 35 U.S.C. 154(b) by 666 days.

(21) Appl. No.: 15/044,191

(22) Filed: Feb. 16, 2016

(65) Prior Publication Data

US 2016/0235938 A1 Aug. 18, 2016

Related U.S. Application Data

(60) Provisional application No. 62/116,733, filed on Feb. 16, 2015.

(51) Int. Cl.
*A61M 16/08* (2006.01)
*A61M 16/06* (2006.01)
*A61M 16/04* (2006.01)

(52) U.S. Cl.
CPC ...... *A61M 16/085* (2014.02); *A61M 16/0495* (2014.02); *A61M 16/06* (2013.01); *A61M 16/0672* (2014.02); *A61M 16/0816* (2013.01); *A61M 16/0493* (2014.02); *A61M 16/0683* (2013.01); *A61M 2202/0208* (2013.01); *A61M 2209/06* (2013.01); *A61M 2230/432* (2013.01)

(58) Field of Classification Search
CPC .. A61M 16/00; A61M 16/04; A61M 16/0463; A61M 16/0816; A61M 16/0841; A61M 16/085; A61M 2025/022; A61M 39/10; A61B 5/097
See application file for complete search history.

(56) References Cited

U.S. PATENT DOCUMENTS

| | | | | |
|---|---|---|---|---|
| 4,045,058 A | * | 8/1977 | Eross | A61M 16/0463 128/207.14 |
| 4,221,130 A | * | 9/1980 | Burrows | A61B 5/083 73/863.58 |
| 4,294,250 A | * | 10/1981 | Dennehey | A61M 39/10 604/403 |

(Continued)

FOREIGN PATENT DOCUMENTS

WO WO-8907956 A1 * 9/1989 ........ A61M 16/0488

*Primary Examiner* — Kathryn E Ditmer
(74) *Attorney, Agent, or Firm* — Vorys, Sater, Seymour & Pease LLP; Rex W. Miller, II

(57) ABSTRACT

A system for delivering oxygen to a patient through an airway includes an airway connector and a nasal cannula holder. The airway connector includes a first connector portion configured to be inserted into the airway, a second connector portion having an open end opposite the first connector portion, and a sample port disposed in a side of the second connector portion. The nasal cannula holder includes a first holder portion configured to connect to the second portion of the airway connector, a second holder portion connected to the first holder portion, and a nasal cannula port disposed in a side portion of the second holder portion configured to receive the nasal prongs of a nasal cannula to deliver oxygen to the patient.

11 Claims, 7 Drawing Sheets

(56) References Cited

U.S. PATENT DOCUMENTS

| | | | | |
|---|---|---|---|---|
| 4,506,665 A | * | 3/1985 | Andrews | A61M 16/08 |
| | | | | 128/202.27 |
| 4,558,709 A | * | 12/1985 | Aida | A61B 5/097 |
| | | | | 600/532 |
| 4,815,459 A | * | 3/1989 | Beran | A61B 5/097 |
| | | | | 128/207.14 |
| 5,060,646 A | * | 10/1991 | Page | A61M 16/0463 |
| | | | | 128/200.26 |
| D355,484 S | * | 2/1995 | Rinehart | D24/110.1 |
| 8,220,461 B1 | * | 7/2012 | Guerra | A61M 16/0463 |
| | | | | 128/200.26 |
| 8,677,999 B2 | * | 3/2014 | Allum | A61M 16/04 |
| | | | | 128/204.25 |
| 2012/0055482 A1 | | 3/2012 | Wilkinson | |
| 2012/0125338 A1 | | 5/2012 | Yarahmadi | |
| 2013/0060157 A1 | | 3/2013 | Beard | |
| 2013/0239970 A1 | * | 9/2013 | Pizzini | A61M 16/0666 |
| | | | | 128/205.22 |

* cited by examiner

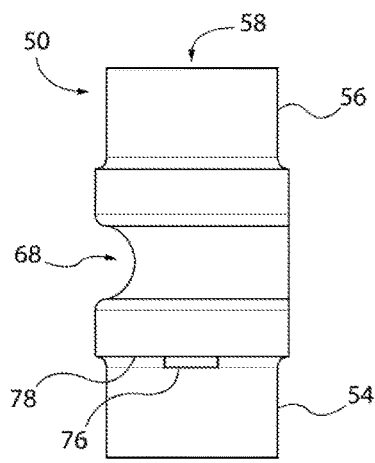
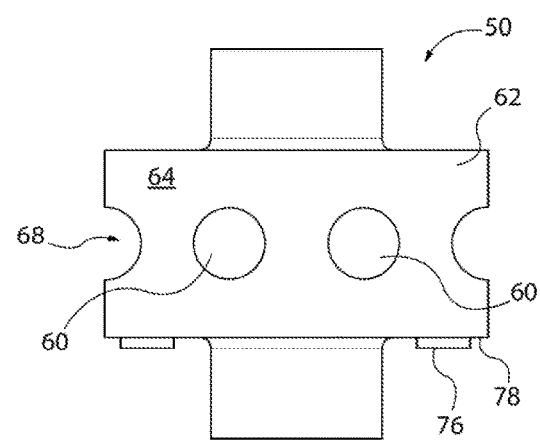
FIG. 10     FIG. 11
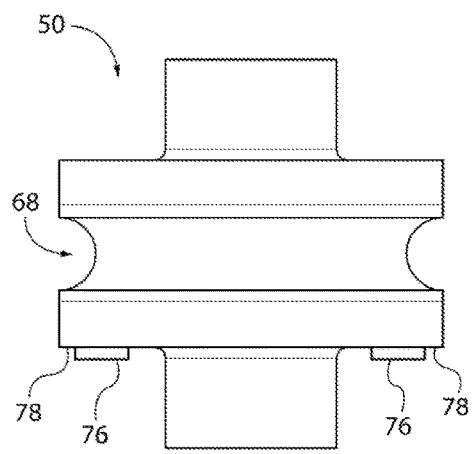
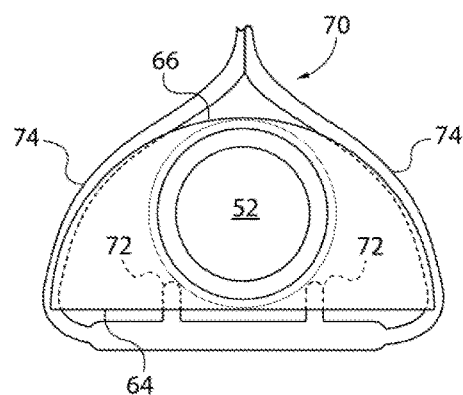
FIG. 12     FIG. 13

OXYGEN DELIVERY AND VENTILATION MONITORING SYSTEMS

CROSS-REFERENCE TO RELATED APPLICATIONS

This application claims priority to U.S. Provisional Patent Application No. 62/116,733, filed on Feb. 16, 2015, the disclosure of which is incorporated herein by reference in its entirety.

TECHNICAL FIELD

The subject matter disclosed herein relates to systems and methods delivering oxygen to a patient and measuring end tidal carbon dioxide.

DISCUSSION OF ART

Patients under moderate or deep sedation for surgical or endoscopic procedures frequently experience obstruction of their upper airway caused by relaxation of pharyngeal muscles and the tongue. Obstruction of the upper airway causes cessation of ventilation, which leads to decreased oxygen saturation and buildup of carbon dioxide ($CO_2$). Prolonged cessation of ventilation can lead to hypoxia or death. An oral airway is a device inserted into the mouth in order to relieve the obstruction of the upper airway caused by the tongue. The oral airway moves the tongue anteriorly to relieve obstruction. The commonly used Guedel type oral airway contains a central orifice for ventilation. As used herein, the term "oral airway" refers to an oropharyngeal airway, which may also be known as an OPA or Guedel pattern airway. A nasal airway is a similar device inserted into a nostril in order to relieve obstruction of the upper airway. Similar to the oral airway, the nasal airway contains a central orifice for ventilation. As used herein, the term "nasal airway" refers to a nasopharyngeal airway, also known as an NPA or nasal trumpet.

End tidal $CO_2$ ($ETCO_2$) monitoring or capnography is used to detect and measure exhaled $CO_2$. Continuous monitoring of $ETCO_2$ has been recommended to monitor adequacy of ventilation in patients during moderate or deep sedation.

A nasal cannula is a commonly used device used to deliver oxygen through the nares. Some patients under moderate or deep sedation, however, will primarily breathe through their mouth and not their nose. For such patients, a facemask may be used to deliver oxygen, and is suitable for patients who are mouth or nose breathers. In addition, a facemask may be able to deliver a higher concentration of oxygen than a nasal cannula. Current oxygen facemasks use oxygen tubing that is attached to the facemask. The facemask is placed on the patient's face and the oxygen tubing is connected to an oxygen source, such as wall oxygen, an anesthesia machine, or a portable oxygen tank. These types of existing oxygen masks are also raised to fit over the patient's nose, but they follow the contour of the face and step down to fit closer over the mouth. This configuration limits the volume within the facemask. In addition, currently available facemasks, place the oxygen source and $ETCO_2$ sampling locations adjacent to each other restating in dilution of the exhaled $CO_2$ and reduced accuracy of the $CO_2$ measurement.

In view of the limitations of the currently available systems, there remains a need for improved systems and methods for delivering oxygen and measuring $ETCO_2$.

BRIEF DESCRIPTION

Presently disclosed is a system for delivering oxygen to a patient through an airway. In embodiments, the system includes an airway connector having a first connector portion configured to be inserted into the airway, a second connector portion connected to the first portion, the second portion having an outer diameter greater than the outer diameter of the first connector portion and having an open end opposite the first connector portion configured to provide an open conduit for ventilation into the airway, and a sample port disposed in a side portion of the second connector portion, wherein the sample port is in fluid communication with the airway and is further configured to receive an $ETCO_2$ sample line from an anesthesia machine. In embodiments, the system also includes a nasal cannula holder having a first holder portion configured to connect to the second portion of the airway connector, wherein at least a portion of the first holder portion has an outer diameter less than an inner diameter of the second connector portion of the airway connector, a second holder portion connected to the first holder portion, the second holder portion configured to provide an open conduit for ventilation into the airway through the airway connector, and a nasal cannula port disposed in a side portion of the second holder portion, wherein the nasal cannula port is in fluid communication with the airway and is further configured to receive the nasal prongs of a nasal cannula to deliver oxygen to the patient.

In some embodiments, the outer diameter of the first connector portion is tapered such that the outer diameter of the first connector portion decreases from adjacent the second connector portion to an end of the airway connector opposite the second connector portion.

In some embodiments, the airway connector includes a radial flange extending perpendicularly to a passageway between the lower portion and the upper portion. In some embodiments, the outer diameter of the flange is equal to the outer diameter of the second connector portion at the flange, and the inner diameter of the flange is equal to the outer diameter of the first connector portion at the flange.

In some embodiments, the airway connector includes at least one spacer configured to maintain a gap between the airway connector and the airway. In some embodiments, the at least one spacer is a pair of axial protrusions extending from a radial edge between the first connector portion and the second connector portion, a plurality of radially extending ridges on a radial edge between the first connector portion and the second connector portion, or a radially enlarged ring disposed between the first connector portion and the second connector portion.

In some embodiments, the outer diameter of the first holder portion tapers from adjacent the second holder portion to an end of the nasal cannula holder configured to be inserted into the second connector portion of the airway connector.

In some embodiments, the second holder portion has a circular cross-section and the nasal cannula port is an arcuate opening in a side wall of the second holder portion extending between 90° and 180° around the circumference of the second holder portion.

In some embodiments, the nasal cannula port includes a gasket around the perimeter of the nasal cannula port configured to inhibit the flow of oxygen out of the passageway through the nasal cannula port around the nasal cannula prongs.

In some embodiments, at least a portion of the nasal cannula holder includes a D-shape cross-section with a flat section and a curved section, and the nasal cannula port is disposed in the flat section. In some embodiments, the nasal cannula holder includes at least one groove in the curved section configured to receive a tube extending from the nasal prongs of the nasal cannula. In some embodiments, the nasal cannula holder has at least one clip configured to secure the nasal cannula to the nasal cannula holder to inhibit separation of the nasal cannula during use. In some embodiments, the nasal cannula port includes a pair of openings each configured to receive one nasal prong of the nasal cannula.

In some embodiments, the nasal cannula holder includes at least one spacer configured to maintain a gap between the nasal cannula holder and the airway or the airway connector. In some embodiments, the at least one spacer is at least two axial protrusions extending from a radial edge between the first holder portion and the second holder portion.

Also disclosed is a kit that includes a plurality of airways of different sizes, a plurality of airway connectors, wherein the first connector portion of each airway connector is sized to cooperate with a given size oral airway, and the second connector portions of the plurality of airway connectors are the same size, and a plurality of nasal cannula holders, each having a first holder portion sized to cooperate with the second connector portions of the plurality of airway connectors.

Also disclosed is a method of delivering oxygen to a patient through an airway that includes the steps of: providing a system for delivering oxygen to a patient through an airway comprising an airway connector and a nasal cannula holder, inserting a first connector portion of the airway connector into the airway to frictionally engage the airway connector to the airway such that a sample port disposed in a side portion of a second connector portion of the airway connector is in fluid communication with the airway, inserting a first holder portion of the nasal cannula holder into an open end of a second connector portion of the airway connector to frictionally engage the nasal cannula holder to the airway connector such that a nasal cannula port disposed in a side portion of a second holder portion is in fluid communication with the airway, inserting the nasal prongs of a nasal cannula into the nasal cannula port of the nasal cannula holder to frictionally engage the nasal cannula to the nasal cannula holder, connecting an ETCO2 sample line to the sample port of the airway connector, and delivering oxygen to the patient from the nasal cannula through the nasal cannula holder, the airway connector and the airway when the patient inhales, and monitoring ETCO2 from the sample port of the airway connector when the patient exhales.

Also disclosed is a facemask for delivering oxygen to a patient that includes a shell configured to be applied over a patient's nose and mouth to define a volume for an oxygen reservoir to be inhaled, an oxygen delivery port on a superior portion of the shell configured to receive a flow of oxygen from an oxygen source, and an exhalation port on an inferior portion of the shell configured to vent exhalation out of the facemask wherein the exhalation portion further comprises a sample port configured to receive an ETCO2 sample line from an anesthesia machine.

In some embodiments, the facemask further includes an elastic strap configured to secure the facemask to a patient, and the shell further includes a pair of elastic strap holders disposed on opposite sides of the shell to receive the elastic strap. In some embodiments, the shell has a front portion that extends substantially linearly in front of the patient's nose and mouth. In some embodiments, the inferior portion of the shell has a depth at least as great as the depth of the superior portion of the shell. In some embodiments, the superior portion and inferior portion form a concave profile from the oxygen delivery port to the exhalation port. In some embodiments, the shell has a volume of at least 300 cc. In some embodiments, the oxygen delivery port has a circular profile and is configured to receive a nasal cannula holder having an output port. In some embodiments, the oxygen delivery port includes a plurality of fenestrations configured to disperse a flow of oxygen into the facemask. In some embodiments, the facemask further includes an oxygen delivery adapter comprising an input port configured to receive an oxygen supply line, and an output port configured to mate with the oxygen delivery port of the facemask to deliver oxygen to the patient.

BRIEF DESCRIPTION OF THE DRAWINGS

Reference is made to the accompanying drawings in which particular embodiments and further benefits of the invention are illustrated as described in more detail in the description below, in which:

FIG. 10 is side view of another embodiment of a nasal cannula holder;

FIG. 11 is a front view of the nasal cannula holder of FIG. 10;

FIG. 12 is a back view of the nasal cannula holder of FIG. 10;

FIG. 13 is a top view of the nasal cannula holder of FIG. 10;

DETAILED DESCRIPTION

Referring generally to FIGS. 1-26, presently disclosed are improved systems for delivering oxygen. The present disclosure also relates to improved systems for monitoring ETCO2 either alone or in combination with oxygen delivery.

Figure 1:
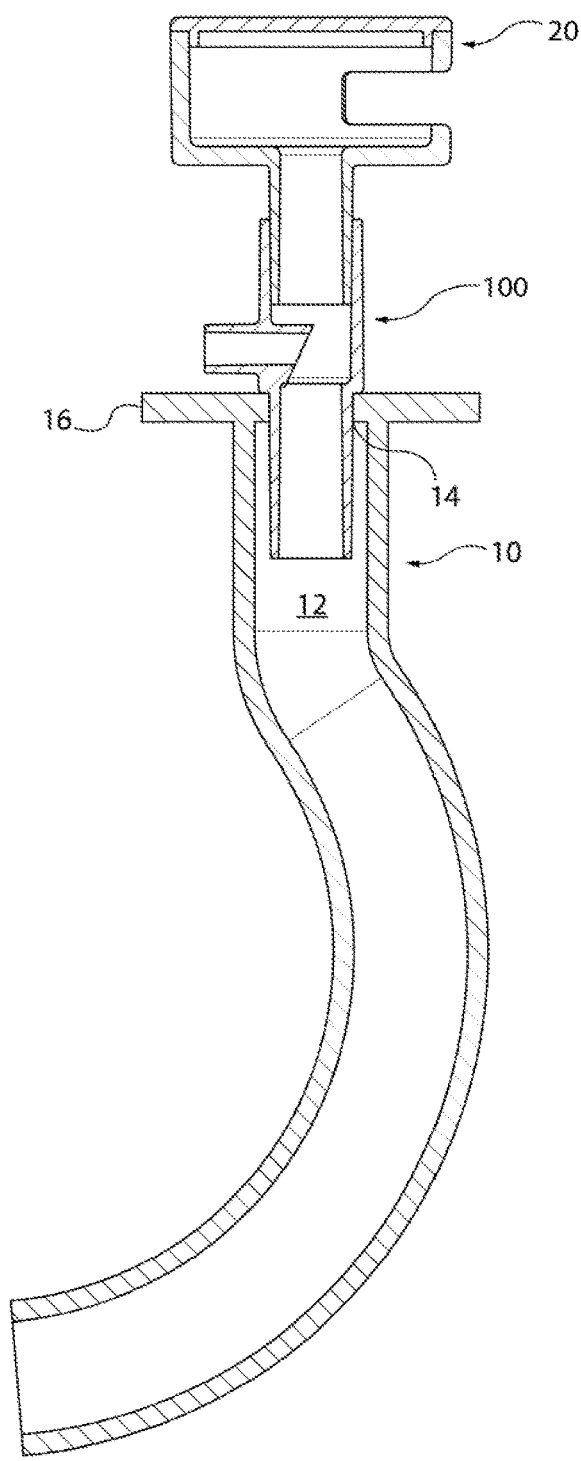
FIG. 1 is a cross-section view of a system for delivering oxygen to a patient through an oral airway.
Figure 2:
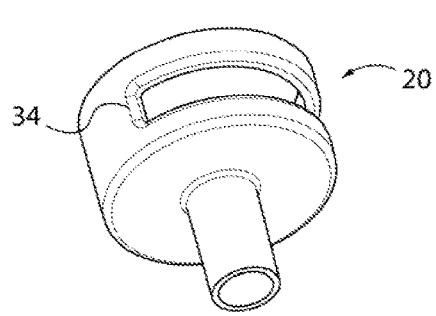
FIG. 2 is an isometric view of an embodiment of a nasal cannula holder.
Figure 3:
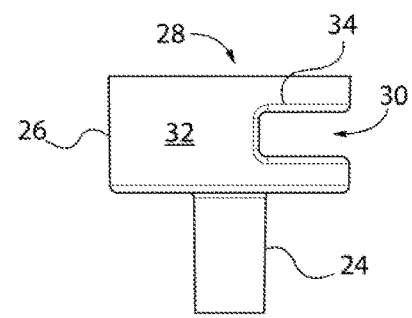
FIG. 3 is a side view of the nasal cannula holder of FIG. 2.
Figure 4:
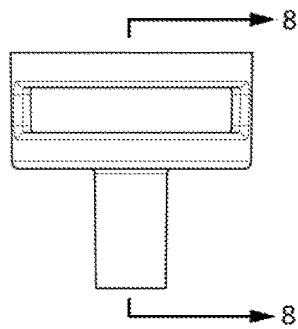
FIG. 4 is a front view of the nasal cannula holder of FIG. 2.
Figure 5:
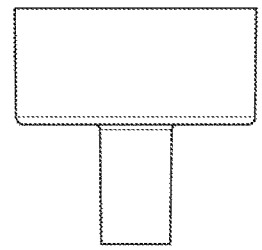
FIG. 5 is a back view of the nasal cannula holder of FIG. 2
Figure 6:
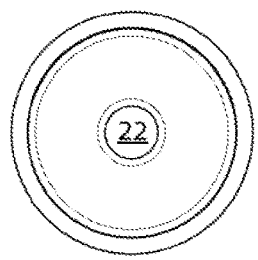
FIG. 6 is a top view oldie nasal cannula holder of FIG. 2.
Figure 7:
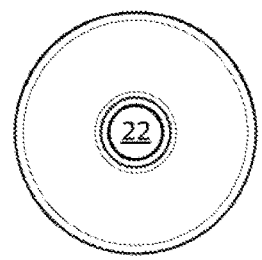
FIG. 7 is a bottom view of the nasal cannula holder of FIG. 2.

Referring now to FIG. 1, a system is disclosed that includes an oral airway 10, a nasal cannula holder 20, and an airway connector 100. The oral airway 10 is a Guedel type oral airway configured to be inserted into a patient's mouth to maintain a clear airway. The oral airway 10 includes a central passageway 12 that extends from the orifice 14 in the flange 16 to the opposite end of the airway. The flange 16 extends radially to limit the penetration of the airway 10 into the patient. As illustrated, the airway connector 100 is connected to the central orifice 14 of the airway 10. The airway connector may be partially inserted through the central orifice and rest against the flange 16 of the airway 10 to prevent the airway connector from sliding completely into the central passageway 12. The nasal cannula holder 10 is connected to the airway connector 100. As further explained below, the nasal cannula holder, the airway connector and the oral airway define a passageway for ventilation and through which oxygen may be delivered to a patient. For purposes of illustration, the nasal cannula holder and airway connector are illustrated for use with an oral airway, but are not so limited. The disclosed nasal cannula holder and airway connector are also configured for use with nasal airways, or other similar airway maintenance devices.

Referring now to FIGS. 2-8, an embodiment of a nasal cannula holder 20 is disclosed. The nasal cannula holder 20 defines a passage 22 through which oxygen is delivered to a patient. In some embodiments, the nasal cannula holder 20 may be used in combination with an airway and airway connector, as illustrated in FIG. 1, in which case both inhalation and exhalation may occur through the nasal cannula holder. The nasal cannula holder 20 has a lower portion 24 and an upper portion 26. The lower portion 24 is configured to be connected to the upper portion of an airway connector. In other embodiments, the lower portion may be configured to be connected to an oxygen delivery facemask. If different sizes are desired, the lower portion may be sized to mate with corresponding sizes of the airway connector and/or oxygen delivery facemask and function as part of a kit. In other embodiments, the lower portion of the nasal cannula holder 10 has a standard size and is compatible with a range of airway connectors and/or oxygen delivery facemasks, each of which have standardized openings for receiving the nasal cannula holder.

The upper portion 26 of the nasal cannula 20 includes an opening for ventilation. The opening may be an open top 28 to provide an open conduit for ventilation to occur through the nasal cannula holder 20, an airway connector, and an airway, or through an endotracheal tube or laryngeal mask airway (LNA). The open top 18 may be configured to receive a cap (such as the cap 40 shown in FIG. 9). When the top 28 is closed by a cap, the nasal cannula holder may at least partially inhibit exhalation through the nasal cannula holder, and exhalation may be vented through another port or opening. In some embodiments, even with the top 28 closed by a cap, exhalation may be sufficiently vented through the nasal cannula holder.

The nasal cannula holder 20 also includes a nasal cannula port 30 configured to receive the nasal prongs of a nasal cannula to delivery oxygen to the patient. In some embodiments, the nasal cannula port 30 is disposed on a side portion 32 of the nasal cannula holder 20. As illustrated, the upper portion 28 has a generally circular cross-section, and the nasal cannula port 30 is a single opening into which both nasal prongs of a nasal cannula are placed. For example, the nasal cannula port 30 may be an arcuate opening extending between 90° and 180° around the circumference of the upper portion 26. The height of the arcuate opening may be approximately equal to the size of the nasal prongs of a nasal cannula so as to frictionally retain the nasal prongs in the opening. In other embodiments, the nasal cannula port may include two openings, one for each of the nasal prongs of the nasal cannula. When the nasal prongs are inserted into the nasal cannula port, the flow of oxygen from the nasal cannula enters the passageway 22 and may be inhaled by the patient. In some embodiments, the nasal cannula port 20 may have a gasket extending around the perimeter 34 of the port to reduce or inhibit oxygen from leaking past the nasal prongs, or to frictionally engage the nasal prongs to retain the nasal prongs in the nasal cannula port.

Figure 8:
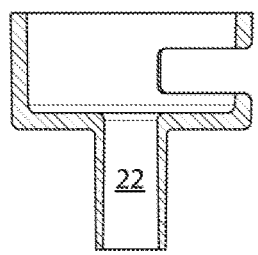
FIG. 8 is a cross-section view of the nasal cannula holder of FIG. 2 taken along section line 8-8.
Figure 9:
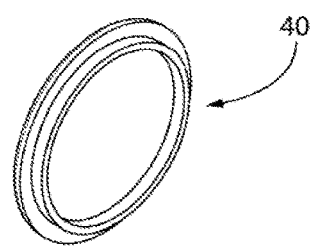
FIG. 9 is an isometric view of a cap for use with the nasal cannula holder of FIG. 2.
Figure 14:
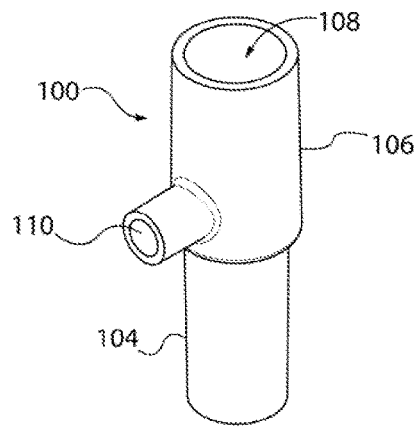
FIG. 14 is an isometric view of an embodiment of an airway connector.
Figure 15:
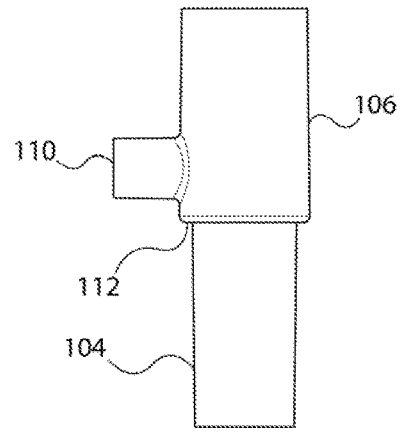
FIG. 15 is a side view of the airway connector of FIG. 14.
Figure 16:
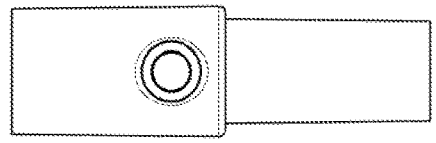
FIG. 16 is a front view of the airway connector of FIG. 14.
Figure 17:
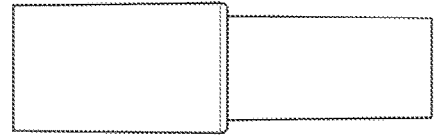
FIG. 17 is a back view of the airway connector of FIG. 14.
Figure 18:
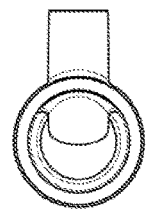
FIG. 18 is a top view of the airway connector of FIG. 14.
Figure 19:
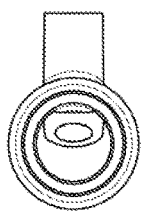
FIG. 19 is a bottom view of the airway connector of FIG. 14.

Referring to FIG. 8, a cross-section of the nasal cannula holder 20 is illustrated. The outer diameter of the lower portion 24 is tapered decreasing towards the end of the nasal cannula holder. The tapered configuration of the lower portion may assist with inserting and retaining the nasal cannula holder in an airway connector. For example, the outer diameter of the lower portion may taper from a diameter greater than the inner diameter of the upper portion of the airway connector to a diameter smaller than the inner diameter of the upper portion of the airway connector so that the nasal cannula holder achieves a wedge fit into the airway connector.

Referring now to FIGS. 10-13, another embodiment of a nasal cannula holder 50 is illustrated. The nasal cannula 50 has a passageway 52 defined by a lower portion 54 and an upper portion 56 substantially as described above. The nasal cannula further includes a D-shaped section configured to receive the nasal cannula. The D-shaped section may be between the lower portion and upper portion, or may be a section of the lower or upper portion. As illustrated in FIG. 13, the D-shaped section has a generally flat section 54 in combination with a generally curved section 56. The nasal cannula port 60 is disposed on the flat section 54, and the nasal prongs 72 of the nasal cannula 70 may extend through the nasal cannula port 60. In some embodiments, the nasal prongs 72 may extend into the passageway 52 as shown in FIG. 13. In other embodiments, the nasal prongs 72 will not extend into the passageway 52, but, in either case, the nasal prongs will be in fluid communication with the passageway 52 to enable oxygen to be delivered to the patient. The flat section 54 may include a slight curve, such as to imitate the general shape of a person's nose, to accommodate the configuration of a nasal cannula.

The nasal cannula holder 50 may also include one or more grooves 58 configured to receive the tube 74 of the nasal cannula 70. As illustrated in FIGS. 11-12, the groove 58 may begin on the flat section 54 (as shown in FIG. 11), and extend at least partially around the curved section 56. In some embodiments, the groove 58 extends completely around the curved section 56. The groove 58 is generally positioned in line with the nasal cannula port 60. In use, the groove 58 may facilitate retention of the nasal cannula 70 on the nasal cannula holder 50. A nasal cannula 70 may include a sliding connector joining the tube 74 on either side of the nasal cannula prongs 72. The sliding connector may be advanced to adjacent the nasal cannula holder 50 to further secure the nasal cannula to the nasal cannula holder. In other embodiments, the nasal cannula holder 50 may include a clip (not shown), which is configured to secure the nasal cannula to the nasal cannula holder and inhibit unintended separation.

The lower portion 54 and upper portion 56 of the nasal cannula holder 50 may be sized to connect to an airway, an airway connector, a facemask, or other ventilation equipment or connectors. In one embodiment, the lower portion and upper portion are each tapered such that the nasal cannula holder may be inserted in an existing connection in a ventilation circuit to allow delivery of oxen with a nasal cannula.

In some embodiments, it may be desired to prevent the nasal cannula holder from completely occluding the airway or the airway connector into which the nasal cannula holder is inserted. In such embodiments, the nasal cannula bolder 50 may also include one or more spacers configured to maintain a gap between the upper portion 56 of the nasal cannula holder and the airway or the airway connector. In one embodiment, the spacers are a pair of axial protrusions 76 extending from a radial flange 78 between the upper portion and the lower portion, such as illustrated in FIGS. 10-13. In other embodiments, the spacers may include a plurality of radially extending ridges on the radial flame between the upper portion and the lower portion. In yet another embodiment, the spacers may include a radially enlarged ring disposed between the upper portion and the lower portion, which also prevents the nasal cannula holder from being inserted too far into the airway or the airway connector.

Referring now to FIGS. 14-20, an embodiment of an airway connector 100 is disclosed. The airway connector 100 is configured to cooperate with an airway, such as the commonly used Guedel airway or nasal trumpet. The presently disclosed airway connector 100 is further configured to enable the delivery of oxygen and the measurement of ETCO2 when using an airway.

As shown in FIG. 14-20, the airway connector 100 includes a passageway 102 for ventilation extending through an upper portion 106 and a lower portion 104. The passageway 102 may also be used to deliver oxygen to a patient through an airway. The lower portion 104 of the airway connector 100 is configured to be inserted into an airway to facilitate interoperability with other medical equipment. In other embodiments, the lower portion 104 may be configured to mate with the airway without being inserted. Airways are available in various sizes and the appropriate size is selected to best fit a given patient. Embodiments of the airway connector 100, and particularly the lower portion 104, may likewise be made in different sizes corresponding to the sizes of the oral airways. The lower portion 104 may generally have a circular cross-section. The length of the lower portion may be selected to extend a sufficient distance into the oral airway to provide a secure connection, while not extending so far as to interfere with the operation of the oral airway. In some embodiments, the outer diameter of the lower portion 104 is tapered. The tapered lower portion may achieve a wedge fit to assist in securing the airway connector in the airway and may further enable a single airway connector to be used with two or more airways of different sizes.

The airway connector 100 also has an upper portion 106. The upper portion 106 includes an open top 108 configured to provide an open conduit for ventilation into the airway. In some embodiments, the top 108 of the airway connector has a standard cross-section and dimension to provide connection to an endotracheal tube or laryngeal mask airway. In this manner, ventilation equipment, such as an anesthesia machine circuit, may be connected to the airway via the airway connector.

The airway connector 100 also includes a sample port 110 configured to receive an ETCO2 sample line from an anesthesia machine. The ETCO2 sample line connected to the sample port 110 permits measuring CO2 levels in the exhalation of patients using an oral airway. By positioning the sample port 110 near the oral airway, and away from the oxygen delivery source, the exhalation is less diluted by the oxygen being delivered allowing for increased accuracy in the ETCO2 measurement. The sample port 110 may extend from a side of the upper portion 106 of the oral airway connector 100 as illustrated in FIGS. 14-20. In one embodiment, the sample port 110 is cylindrical and configured to receive and retain a tube with a frictional engagement. The inner diameter of the sample port 110 may be approximately equal to the outer diameter of the tube. In other embodiments, the sample port 110 may be threaded to receive a threaded connector attached to a CO2 sample line. In any case, the sample port 110 provides fluid communication between the passageway of the airway connector and an ETCO2 sample line. In some embodiments, the airway connector may include a length of tubing attached to the sample port so as to permit use of the airway connector under an oxygen delivery facemask, while allowing the ETCO2 connection to be provided outside the facemask.

The airway connector 100 may also include a radial flange extending perpendicularly to the passageway between the lower portion 104 and the upper portion 106. As shown, the radial flange is formed by the difference in the outer diameters of the lower portion and upper portion of the airway connector. The radial flange 112 may be sized such that when the lower portion 104 of the airway connector 100 is inserted into the airway, the radial flange 112 rests on a flange of the airway. In this manner, the radial flange 112 prevents further insertion of the airway connector. In other embodiments, the flange may have an outer diameter greater than the outer diameter of both the lower portion or the upper portion, and in such embodiments, the outer diameter of the lower portion and the upper portion may be the same.

Figure 20:
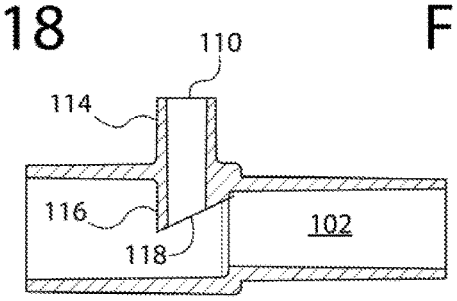
FIG. 20 is a cross-section view of the airway connector of FIG. 14 taken along section line 20-20.

As shown in FIG. 20, in some embodiments, the sample port 110 has an exterior portion 114 that extends outward from the side of the airway connector 100. The exterior portion 114 is configured to receive an ETCO2 sample line from anesthesia machine as described above. The sample portion 110 also includes an interior portion 116 that extends inward from the side of the airway connector into the passageway 102 of the airway connector. The interior portion 116 terminates in an opening 118 that is oriented toward the first portion of the airway connector. As shown in FIG. 20, the opening is angled towards the first portion of the airway connector at approximately 45. When a patient exhales, the exhalation passes through the airway into the lower portion of the airway connector, and up through the airway connector. The angled opening of the interior portion of the sample port catches a portion of the patient's exhalation, and directs that portion of the exhalation through the sample portion and to an ETCO2 sample line connected to the exterior portion to be measured. In contrast, when a patient inhales, the inhalation draws air and, optionally supplemental oxygen, in through the upper portion of the airway connector. The angled portion of the interior portion of the sample portion shields the sample portion from such inhalation and supplemental oxygen thereby reducing dilution of the exhalation and improving the accuracy of the ETCO2 measurement addition, when the airway connector is used in combination with a nasal cannula holder to supply a continuous flow of supplemental oxygen, the angled opening reduces the ingress of the supplemental oxygen into the sample port during exhalation, which also improves the accuracy of the ETCO2 measurement.

Figure 21:
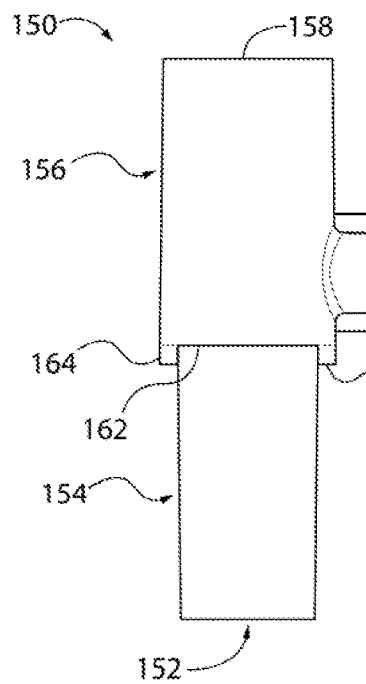
FIG. 21 is a side view of another embodiment of an airway connector.
Figure 22:
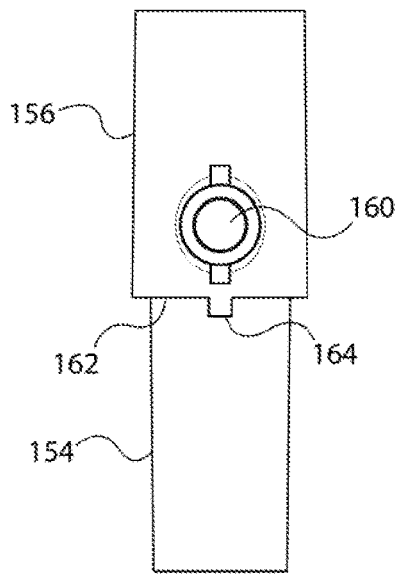
FIG. 22 is a front view of the airway connector of FIG. 21.
Figure 23:
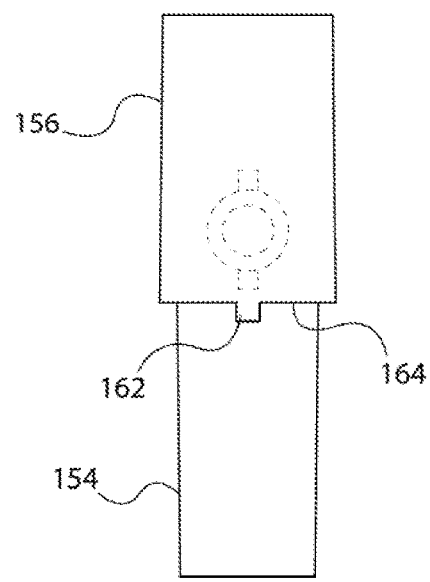
FIG. 23 is a back view of the airway connector of FIG. 21.

Referring now to FIGS. 21-23, another embodiment of an airway connector 150 is illustrated. The airway connector 150 has a passageway 152 defined by a lower portion 154 and an upper portion 156 with an open top 158 substantially as described above. In some embodiments, it may be desired to prevent the airway connector from completely occluding the airway. In such embodiments, the airway connector 150 may also include one or more spacers configured to maintain a gap between the airway connector and the airway. In one embodiment, the spacers are a pair of axial protrusions 164 extending from the radial flange 162 between the upper portion and the lower portion, such as illustrated in FIGS. 21-23. In other embodiments, the spacers may include a plurality of radially extending ridges on the radial flange between the upper portion and the lower portion. In yet another embodiment, the spacers may include a radially enlarged ring disposed between the upper portion and the lower portion, which also prevents the airway connector from being inserted too far into the airway.

The airway connector and the nasal cannula holder, as previously described, may be used in combination to deliver oxygen to a patient, while also monitoring ETCO2. The airway connector is inserted into an airway, and an ETCO2 sample line is connected to the sample port 62. The lower portion of the nasal cannula holder may then be inserted into the open top of the upper portion of the airway connector, and a nasal cannula attached to the nasal cannula port. Oxygen is then delivered by the nasal cannula, through the nasal cannula port and into the combined passageway through the nasal cannula holder and airway connector. Upon inhalation, a patient will receive the oxygen delivered by the nasal cannula. Upon exhalation, the ETCO2 may be measured through the sample port, while the exhalation is vented. By positioning the sample port closer to the patient than the nasal cannula port, the oxygen delivered through the nasal cannula port has little to no impact on the exhalation and the accuracy of the ETCO2 measurement may be improved.

Also disclosed is a kit including a plurality of oral airways of different sizes. The kit also includes a plurality of airway connectors as described above. The lower portion of each airway connector is sized to cooperate with one or more of the different sized oral airways. The upper portion of each airway connector may be the same size, which may be a standardized size for use with other ventilation equipment. The kit also includes one or more nasal cannula holders as described above, which are sized to cooperate with the plurality of airway connectors. The combination of oral airways, airway connectors, and nasal cannula holders form a system for delivering oxygen and measuring ETCO2 of patients using an oral airway. In other embodiments, the kit may include a plurality of nasal airways, airway connectors and nasal cannula holders to form a system for delivering oxygen and measuring ETCO2 of patients using a nasal airway.

Figure 24:
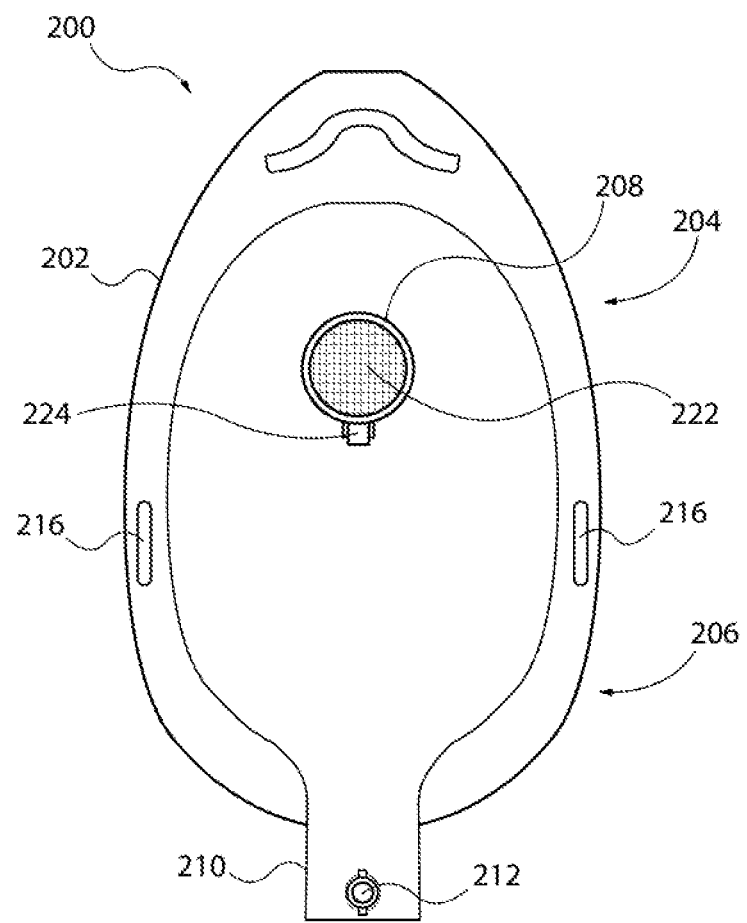
FIG. 24 is a front view of an embodiment of an oxygen delivery facemask.
Figure 25:
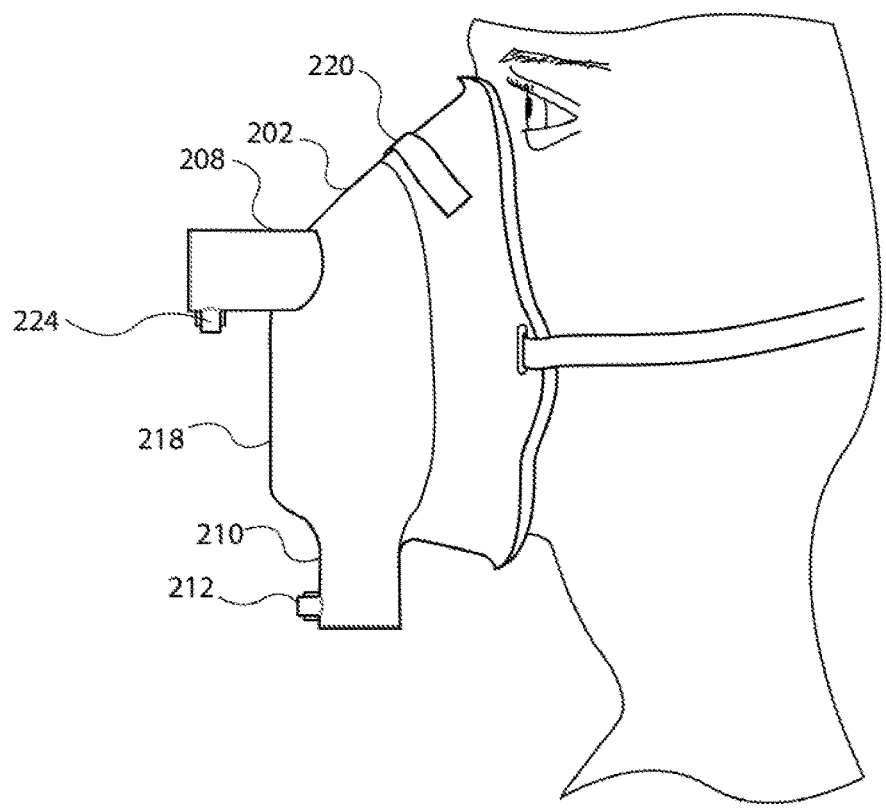
FIG. 25 is a side view of an embodiment of an oxygen delivery facemask.
Figure 26:
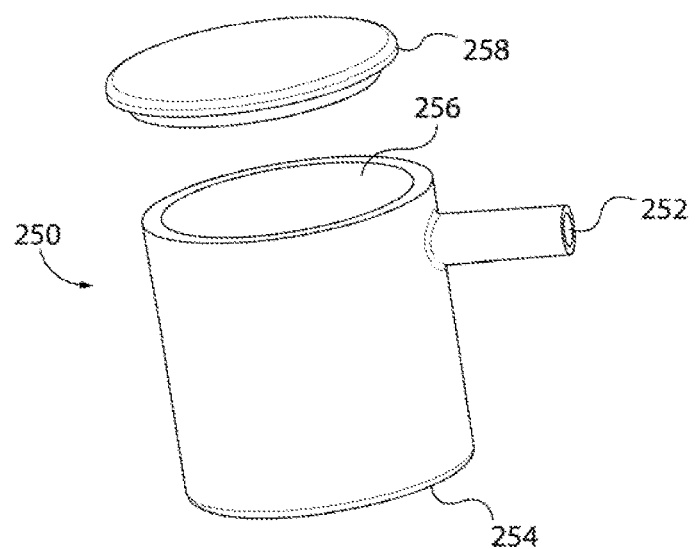
FIG. 26 is a side view of an oxygen delivery adapter for use with the oxygen delivery facemask.

Referring now to FIGS. 24-26, an embodiment of an oxygen delivery facemask is disclosed. The facemask 200 provides for both improved oxygen delivery and ETCO2 monitoring capabilities. As shown in FIGS. 24-25, the facemask 200 includes a shell 202 configured to be applied over a patient's nose and mouth. The shell 202 defines a volume within which oxygen is delivered to the patient. The shell 202 may be formed of plastic. In some embodiments, the shell 202 includes a pair of elastic strap holders 216 and the facemask is secured to the patient with an elastic strap. The facemask may also include an adjustable metal nose piece 220, which may be attached to or integral with the shell 202, to better conform the facemask to the patient's face.

The oxygen delivery facemask 200 also includes an oxygen delivery port 208 through which oxygen is received, and an exhalation port 210 to vent the patient's exhalation. In embodiments, the oxygen delivery port 208 is disposed on a superior (upper) portion 204 of the shell 202. As illustrated in FIG. 25, the oxygen delivery port 208 is positioned on the superior portion 204 of the shell just below the patient's nose. As will be apparent, the oxygen delivery facemask 200 may be sized for different size patients, such as children or adults. In embodiments, the exhalation portion is disposed on an inferior (lower) portion 206 of the shell. As illustrated in FIGS. 24-23, the exhalation port 210 extends downward from the inferior portion 206, and is generally positioned below the patient's mouth to vent exhalation out of the facemask.

In order to measure ETCO2, the oxygen delivery facemask also includes a sample port 212. The sample port 212 is configured to receive an ETCO2 sample line from an anesthesia machine. In an embodiment, the sample port 212 is provided on the exhalation port 212. The position of the sample port 212 relative to the oxygen delivery port 208 may improve the accuracy of the ETCO2 measurement as compared to previously available systems. In prior systems, the oxygen delivery and CO2 measurement locations were often positioned adjacent to one another on a facemask resulting in dilution of the exhalation with the delivered oxygen. The presently disclosed oxygen delivery facemask positions the oxygen delivery port 208 further from the sample port 212, thereby reducing such dilution effects and improving the accuracy of the measurement. In other embodiments, the oxygen delivery port 208 and exhalation port 210 may be reversed as deemed clinically beneficial. In such embodiments, the oxygen delivery port 208 and exhalation port 210 may have identical cross-sections permitting interchangeability of connections to either port.

In some embodiments, the oxygen delivery facemask 200 also provides a greater volume than previously available. Current oxygen masks on the market are raised to fit over the nose but then follow the contour of the face and step down to fit closer over the mouth. As illustrated in FIG. 25, the presently disclosed facemask does not step down over the mouth. Rather, the facemask 200 has a front portion 218 that extends substantially linearly through the superior portion 204 and inferior portion 206. In other embodiments, the front portion of the facemask 202 has a substantially concave profile from the oxygen delivery port to the exhalation port. By maintaining the depth of the facemask 200 substantially the same through both the superior portion 204 and inferior portion 206, the facemask 200 has a substantially increased volume relative to previously available products. In use, this increased volume permits more oxygen to accumulate within the facemask to be inhaled by the patient on a subsequent breath. In some embodiments, an adult facemask 202 may have a volume of at least 300 cc.

The oxygen delivery port 208 of the facemask 200 is configured to receive a flow of oxygen from an oxygen source. In an embodiment, the oxygen delivery port 208 has a circular profile and is configured to receive the output port of a nasal cannula holder (such as lower portion 24 shown in FIGS. 2-8). Patients requiring anesthesia often already have a nasal cannula. By using the presently disclosed nasal cannula holder in combination with the oxygen delivery facemask, oxygen may be delivered to the patient through the facemask with the same nasal cannula already in use by the patient. In this manner, patients may be more quickly transitioned into and out of procedures with fewer equipment changes.

In some embodiments, the oxygen delivery port 2 includes a plurality of fenestrations 222. As shown in FIG. 25, the fenestrations are configured to disperse the flow of oxygen into the facemask. Dispersing the flow of oxygen may be more comfortable for the patient by reducing localized pressure or irritation from the oxygen flow. In addition, dispersing the flow of oxygen may further diminish the dilution of exhaled CO2 that would be caused by an undispersed stream of oxygen into the mask. In some embodiments, the fenestrations may be absent to allow passage of nasal gastric tubes through the oxygen delivery port 208.

Although the oxygen delivery facemask 200 has been described in use with a nasal cannula holder, the facemask may also be used with traditional oxygen supply lines. Referring now to FIG. 26, an oxygen delivery adapter 250 is disclosed that includes an input port 252 configured to receive an oxygen supply line, an output port 254 configured to mate with the oxygen delivery port 208 of the facemask 200 to deliver oxygen to the patient. The top 256 of the oxygen delivery adapter 250 is preferably closed to ensure oxygen flows into the facemask through the output port 254. In some embodiments, the top 256 of the oxygen delivery adapter 250 is open but may be sealed with a cap 258. In this manner, the top 256 of the oxygen delivery adapter 250 may be used as a conduit to other ventilation equipment, and capped when not in use. The same cap 258 may be used to close the top of the nasal cannula holder when the nasal cannula holder is used in combination with the facemask, thereby reducing the number of components required in the overall system.

The presently disclosed systems improve the delivery of oxygen and increase the accuracy of the ETCO2 measurement relative to previously available systems. Although described individually, it will be apparent that the presently disclosed systems are usable in various combinations to achieve the improved oxygen delivery and measurement accuracy. For example, in some embodiments, once a decision is made to insert an oral airway and to monitor ETCO2, the oral airway may be inserted into the patient. An oral airway adapter (as described above) may then be inserted into the oral airway and a sample line connected to the sample port to measure ETCO2. Oxygen may then be delivered to the patient through the use of the nasal cannula holder attached to the oral airway adapter, or through the use of an oxygen delivery facemask with or without use of the nasal cannula holder. In this manner, effective oxygen delivery and improved ETCO2 are both achieved using the presently disclosed systems.

In the specification and claims, reference will be made to a number of terms that have the following meanings. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts, while still being considered free of the modified term. Moreover, unless specifically stated otherwise, any use of the terms "first," "second," etc., do not denote any order or importance, but rather the terms "first," "second," etc., are used to distinguish one element from another.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur this distinction is captured by the terms "may" and "may be." The term "instructions" as used herein may refer to computer executable instructions.

This written description uses examples to disclose the invention, including the best mode and also to enable one of ordinary skill in the art to practice the invention, including making and using any devices or systems and performing any incorporated methods. The patentable scope of the invention is defined by the claims and may include other examples that occur to one of ordinary skill in the art. Such other examples are intended, to be within the scope of the claims if they have structural elements that do not different from the literal language of the claims or if they include equivalent structural elements with insubstantial differences from the literal language of the claims.

What is claimed is:

1. A system for delivering oxygen to a patient through an airway comprising:
  an airway connector having
    a first connector portion configured to be inserted into the airway,
    a second connector portion connected to the first connector portion, the second portion having an outer diameter greater than an outer diameter of the first connector portion and having an open end opposite the first connector portion configured to provide an open conduit for ventilation into the airway, and
    a sample port disposed in a side portion of the second connector portion, wherein the sample port is in fluid communication with the airway and is further configured to receive an ETCO2 sample line from an anesthesia machine; and
  a nasal cannula holder having
    a first holder portion configured to connect to the second portion of the airway connector, wherein at least a portion of the first holder portion has an outer diameter less than an inner diameter of the second connector portion of the airway connector,
    a second holder portion connected to the first holder portion, the second holder portion configured to provide an open conduit for ventilation into the airway through the airway connector, and
    a nasal cannula port disposed in a side portion of the second holder portion, wherein the nasal cannula port is in fluid communication with the airway and is further configured to receive nasal prongs of a nasal cannula to deliver oxygen to the patient;

wherein the second holder portion has a circular cross-section and the nasal cannula port is an arcuate opening in a side wall of the second holder portion extending between 90° and 180° around the circumference of the second holder portion.

2. The system of claim 1, wherein the outer diameter of the first connector portion is tapered such that the outer diameter of the first connector portion decreases from adjacent the second connector portion to an end of the airway connector opposite the second connector portion.

3. The system of claim 1, wherein the airway connector comprises a radial flange extending perpendicularly to a passageway between the first connector portion and the second connector portion.

4. The system of claim 3, wherein an outer diameter of the flange is equal to the outer diameter of the second connector portion at the flange, and an inner diameter of the flange is equal to the outer diameter of the first connector portion at the flange.

5. The system of claim 1, wherein the airway connector further comprises at least one spacer configured to maintain a gap between the second connector portion of the airway connector and the airway.

6. The system of claim 5, wherein the at least one spacer comprises a pair of axial protrusions extending from a radial edge between the first connector portion and the second connector portion.

7. The system of claim 1, wherein the sample port portion comprises an exterior portion extending outward from the side portion of the airway connector that is configured to receive the ETCO2 sample line from the anesthesia machine, and an interior portion extending inward from the side portion of the airway connector.

8. The system of claim 7, wherein the interior portion of the sample port terminates in an opening that is angled toward the first portion of the airway connector.

9. The system of claim 1, wherein the outer diameter of the first holder portion tapers from adjacent the second holder portion to an end of the nasal cannula holder configured to be inserted into the second connector portion of the airway connector.

10. The system of claim 1, wherein the nasal cannula port includes a gasket around a perimeter of the nasal cannula port configured to inhibit the flow of oxygen out of the open conduit of the nasal cannula holder through the nasal cannula port around the nasal cannula prongs.

11. A method of delivering oxygen to a patient through an airway comprising:
  providing a system comprising the airway connector and the nasal cannula holder of claim 1;
  inserting the first connector portion of the airway connector into the airway to frictionally engage the airway connector to the airway such that the sample port disposed in the side portion of the second connector portion of the airway connector is in fluid communication with the airway,
  inserting the first holder portion of the nasal cannula holder into the open end of the second connector portion of the airway connector to frictionally engage the nasal cannula holder to the airway connector such that the nasal cannula port disposed in the side portion of the second holder portion is in fluid communication with the airway,
  inserting nasal prongs of a nasal cannula into the nasal cannula port of the nasal cannula holder to frictionally engage the nasal cannula to the nasal cannula holder,
  connecting an ETCO2 sample line to the sample port of the airway connector, and
  delivering oxygen to the patient from the nasal cannula through the nasal cannula holder, the airway connector and the airway when the patient inhales, and monitoring ETCO2 from the sample port of the airway connector when the patient exhales.

\* \* \* \* \*

UNITED STATES PATENT AND TRADEMARK OFFICE
CERTIFICATE OF CORRECTION

PATENT NO. : 10,398,869 B2  
APPLICATION NO. : 15/044191  
DATED : September 3, 2019  
INVENTOR(S) : Babak Khabiri, Nestor Millan Narcelles and Scott Meyers Cooper Page 1 of 1

It is certified that error appears in the above-identified patent and that said Letters Patent is hereby corrected as shown below:

In the Claims

Column 13, Line 28, Claim 7 "port portion" should read --port--.

Signed and Sealed this
Fifth Day of November, 2019

Andrei Iancu
*Director of the United States Patent and Trademark Office*